United States Patent [19]

Lauren

[11] Patent Number: 4,755,593
[45] Date of Patent: Jul. 5, 1988

[54] NOVEL BIOMATERIAL OF CROSS-LINKED PERITONEAL TISSUE

[76] Inventor: Mark D. Lauren, 160 Canning Street, Carlton, Victoria, Australia, 3053

[21] Appl. No.: 888,717

[22] Filed: Jul. 24, 1986

[30] Foreign Application Priority Data

Jul. 24, 1985 [AU] Australia .................. PH1616

[51] Int. Cl.$^4$ .................. A23J 1/10; C09H 1/00
[52] U.S. Cl. .................. 530/356; 128/156; 128/DIG. 8; 514/2; 514/21; 514/801
[58] Field of Search ......... 530/356; 128/156, DIG. 8; 514/2, 21, 801

[56] References Cited

U.S. PATENT DOCUMENTS 4,280,954  7/1981  Yannas et al. .................. 530/356

OTHER PUBLICATIONS

Dale, "Arterial Grafts: 1900-1978", Graft Materials in Vascular Surgery, Year Book Medical Publishers, Chicago, Ill., Ch. 1, pp. 3-12 (1978).
Voorhees, A. B. et al., "Use of Tubes Constructed from Vinyon-N Cloth in Bridging Arterial Defects", Ann. Surg. 135; 332 (1952).
Wright, C. B., ed. Vascular Grafting, John Wright Pub., Littleton, Mass., Section II Large Vessel Grafts, pp. 27-52 (1983).
Dardik, H. et al., "Biodegradation and Aneurysm Formation in Umbilical Vein Grafts," Ann. Surg. 199(1); 61-68 (1984).
Binet, J. P. et al., "Clinical Use of Heterografts for Replacement of Aortic Valve", J. Thorac. Cardiovas. Surg. 55; 238-242 (1968).
Ionescu, M. I. et al, "Heart Valve Replacement with the Ionescu-Shiley Pericardial Xeongraft", J. Thorac. Cardiovas. Surg. 73; 31-42 (1977).
Morse, D. ed., "Guide to Prosthetic Heart Valves", Springer-Verlag, New York (1985), pp. 225-232.
Thuroff, "Transplantation of a Free Peritoneal Patch in Surgery of the Reneal Pelvis and Ureter", Univ. of Mainz, FRG, pp. 304-311.
Yaita, "Use of Free Peritoneal Patch in Reinforcing Alimentary Tract Anastomosis", Japanese Journal of Surgery, vol. 5, No. 1, pp. 56-63, 1975.
Szczurek, "Morphological Studies on the Inner Lining Formed from Free Peritoneal Graft in Aortic Prostheses in Dogs", Polish Medical Journal, vol. X, No. 4/1971, pp. 952-956.
Fadali, "The Use of Autogenous Peritoneum for Heart Valve Replacement", Johns Hopkins, vol. 60, No. 2, 8/70, pp. 189-195.
Flory et al, "Melting Equilibrium for Collagen Fibers Under Stress", J. Am. Chem. Soc., 83:1308-1316 (1961).
Ionescu, M. I. ed., "Tissue Heart Valves", Butterworths, London, 1978, pp. 349-352.
Stegman, H., "Mikrobestimmung von Hydroxyprolin mit Chloramin-T und P-Dimethylaminobenzaldehyde", Z. Physiol. Chem. 187:41 (1958).
Nyilas, E. et al., "Effects of Polymer Molecular Structure and Force-Field Characteristics on Blood Interfacial Pehnomena I", J. Biomed. Mater. Res. Symp., No. 8, pp. 51-68 (1977).

Primary Examiner—Delbert R. Phillips
Assistant Examiner—Nathan M. Nutter
Attorney, Agent, or Firm—Bacon & Thomas

[57] ABSTRACT

A biomaterial suitable for use in medical devices which comprises peritoneal tissue, especially animal parietal peritoneum tissue, which has been chemically treated to crosslink the collagen in the tissue.

13 Claims, No Drawings

NOVEL BIOMATERIAL OF CROSS-LINKED PERITONEAL TISSUE

BACKGROUND OF THE INVENTION

Over the past twenty five years, the quality of life for many people has been dramatically improved due to advances in replacing damaged or diseased organs. Many new materials have been developed for medical applications intended for use in contact with or implanted within the body. e.g. bone and joint replacements, hemodialysis devices, artificial hearts, and soft contact lenses. The overall requirements for such materials are quite demanding. They must function within the body environment, and be stable, non toxic, and not elicit any adverse host reaction. Most are synthetic polymers, while some more recently developed biomaterials consist of chemically modified tissues.

An important distinction must be made between organ transplants and the application of a biomaterial. Transplants consist of viable tissue either autotransplanted within the same organism (e.g. skin grafts or saphenous vein arterial replacements) or used from one organism to another (e.g. kidney or heart transplants). Biomaterials are generally non-viable materials produced in the laboratory and intended for medical device construction.

Both synthetics and tissue based materials have their advantages and disadvantages. The properties of synthetic polymers may be readily modified by altering monomers or reaction conditions. Polymers are easily fabricated and generally have acceptably low biological responses. For critical blood contacting applications however (e.g. small diameter arterial replacement and cardiac valves), plastic materials all exhibit unacceptable thrombogenicity. Tissue biomaterials have shown superior blood contacting properties, but suffer from being more difficult to fabricate into devices and possess inferior in vivo stability. Incomplete crosslinking of these tissues, particularly the collagen matrix, can lead to enhanced biodegradation, antigenicity, and loss of mechanical function.

The current invention addresses these two important aspects of tissue materials: biophysical stability and ease of fabrication. Research was conducted using bovine peritoneum as a tissue source. Methods of achieving greater collagen crosslinking were investigated. To facilitate device construction, a simple method is described for bonding tissue to synthetic substrates. These substrates may be attached to other metal or plastic systems by conventional means.

The processing techniques generally used to produce tissue biomaterials involves stabilizing the structure to prevent resorption and tissue rejection following reimplantation. Stabilization involves crosslinking the collagenous component of the tissue usually using glutaraldehyde (GA). This is a crucial step in the preparation of the biomaterial, as the ultimate fate of the tissue is related to the fixatives, fixation conditions, and the condition of the raw starting material.

It is important to process the tissue while it is still fresh. Autolytic and bacterial degradation can proceed to the point that the tissue may be incapable of being sufficiently stabilized. These effects have generally not received appropriate attention, as current manufacture of tissue materials allows significant latitude in the collection and storage of fresh tissue prior to stabilization.

Early attempts at replacing blood vessels in man involved the use of solid walled rigid tubes of metal and acrylics (1). These grafts did not perform well in most cases. The modern era of synthetic vascular grafts was initiated by the use of Vinyon cloth tubes (2). Present day synthetic grafts are used in diameters down to 6-8 mm and are mainly fabricated from Dacron* polyester fiber and expanded Teflon* (polytetraflouroethylene) (3).
(* Registered Trade Marks)

For arterial replacement below 6-8 mm, biologic vascular grafts have proven more successful. Grafts have been prepared from bovine carotid artery, human umbilical veins, and bovine ureters by a variety of chemical methods. The long term durability of these grafts however is currently an issue of concern, with failure rates and complications rising after 3-5 years (4).

For constructing heart valves and other applications, material in the form of a flat sheet or membrane is required. Stabilized calf and porcine aortic valves were introduced for clinical use in 1965 as an alternate to the more thrombogenic mechanical devices (5). Formalin was used for stabilization, and these valves underwent gross degeneration of the collagen fibers and led to aortic insufficiency. In 1969, GA was introduced as a tanning agent, which proved to be a better stabilizing agent, making the valve tissue pratically inert and nonantigenic. At present, the more commonly used vascular grafts and valve xenografts use GA for their primary fixation.

Pericardium is currently the most widely used xenograft membrane material for cardiovascular applications. The pericardial xenograft valve was introduced in 1974 (6), with several new generation devices at various stages of development including the Hancock, low-profile Ionescu-Shiley, Carpentier-Edwards, and Mitral Medical valves. Despite their superior hydraulic and blood contacting properties, tissue valves continue to have calcification and durability problems (7).

In an effort to reduce or eliminate these complications, research was conducted into finding alternate tissue sources, improved chemical fixation methods, and methods to improve device construction.

The present invention relates to the use of peritoneal tissue for producing a new biomaterial. The materials produced have advantageous biological and structural properties relative to existing xenograft materials; including flexibility and the presence of two smooth surfaces.

It is an object of the invention to provide an improved biomaterial suitable for bioprosthesis fabrication, and methods for producing same.

It is another object to, (1) provide improved methods for collagen crosslinking, and (2) provide methods for producing a composite tissue/synthetic material.

The peritoneum is the largest serous membrane in the body. The membrane lines the abdominal walls (parietal peritoneum) and also invests the contained viscera. The free surface is lined with a single layer of mesothelial cells, lying above an elastic membrane and subjacent connective tissue layers.

Peritoneum has been surgically transplanted into different physiological systems with general success. Free grafts have been used to cover defects in the renal pelvis (8) and to reinforce alimentary trace anastomoses (9). As an aortic patch graft in dogs (10), good healing was observed with no ruptures, occlusions, or aneurysms. Autogenous peritoneum has also been used for cardiac valve replacement in dogs (11). The grafts did not function well in the long term due to thickening and contraction, but did show acceptable short term blood compatibility.

SUMMARY OF THE INVENTION

This invention provides a method for processing animal peritoneal tissue into a biomaterial suitable for use in medical devices, wherein the tissue is chemically treated to crosslink the collagen and make the tissue stable, less antigenic, and sterile.

Also provided by the invention is a simple procedure for bonding synthetic polymers to tissue surfaces. This method produces a membrane material with a blood compatible tissue surface on one side backed with a synthetic substrate. By modifying the substrate, the physical properties of the composite may be changed, e.g. fatigue resistant polymers may be used for producing blood compatible and fatigue resistant materials needed for pulsatile cardiovascular applications.

I

MATERIAL PROCESSING

More specifically, in accordance with the invention, the tissue biomaterial is produced using the following steps:
1. tissue harvesting,
2. mechanical preparation,
3. chemical treatment, and
4. substrate bonding.

These steps are described in more detail as follows:

1. Tissue Harvesting—Peritoneum may be collected from a variety of animal sources; preferably calf or adult bovine. Alternate sources include ovine and porcine. Tissue from younger animals generally contains less fat and is easier to handle than adult tissues.

The tissue should be freshly collected and preferably stored in isotonic salt solution prior to processing. It is important to begin processing as soon as possible following animal slaughter to prevent enzymatic and/or bacterial degradation.

Tissue may be collected from the inferior border of the diaphram muscle. To facilitate removal, the whole muscle may be excised for more careful removal of the peritoneum. By this technique, two lines may be scored through the tissue a fixed distance apart prior to removal from the muscle. This allows the in vivo length to be referenced, so that the appropriate tension may be applied during chemical fixation.

Peritoneal removal may be performed by blunt or sharp dissection, injection of fluid into the intervening space, or through the use of enzymes to loosen the subjacent connective tissue layers.

Large pieces of parietal peritoneum (approximately 20×50 cm) may be obtained from the lateral aspect of the abdominal wall. This is an appropriate source of material for burn or wound covering applications.

(2) Mechanical Preparation—Mechanical preparation involves cleaning and mounting of the tissue prior to chemical treatment. Adherent fatty and muscular tissues are cleared, and the tissue is mounted on a frame. The tissue is preferably fixed at its in vivo dimensions, with both sides exposed to the fixative.

The physical properties of the final material may be changed my tanning the tissue under different strains relative to its in vivo length. Stretching beyond its natural length produces a thinner and stiffer material.

(3) Chemical Treatment—Approximately 5–10 frames are placed in a container and exposed to the processing solutions.

The primary fixation is preferably performed with GA at 0.1–5.0% concentration in phosphate buffered saline (PBS), pH 7.4. Other buffer systems may also be used. Fixation times range from 1–14 days, with longer times having questionable efficacy. It is preferred to tan from 3–5 days. Following all tanning reactions, it is important to rinse the tissue to ensure low levels of residual processing chemicals in the final material.

In aqueous solution, amide bonds may be formed by reaction of carboxyl groups in proteins and amine compounds. By bridging the carboxyl groups of aspartic and glutamic acid with diamine compounds, additional crosslinks to those produced by GA may be formed in the collagen. Control of pH is important, with mild acidity preferred to avoid excessive protonation of the amine and ensure good reaction rates. Diamine tanning may be performed before, along with, or following GA treatment. Both aliphatic and aromatic diamines may be used. Mixtures may be useful in providing a range of chain lengths which increases the probability of bond formation.

It is preferred to follow the diamine reaction with GA to endcap and crosslink any unreacted amines. It is also preferred to follow the GA step with an amino acid solution (e.g. 0.01–0.05M glycine) to cap unreacted aldehyde groups.

The enhanced crosslinking is expected to impart resistance to biodegradation. By capping unreacted groups, the overall host reaction to the implant is expected to be reduced.

Alternate tanning agents may also be used, including formaldehyde, carbodiimides, diisocyanates, or adipic dialdehyde. In addition, enzymes such as ficin and trypsin may be used to increase the flexibility of the tissue. For blood contacting applications, the tissue may be treated with anticalcification agents or antithrombogenic coatings.

Treatment with hydrogen peroxide may be used, preferably in the range of 0.01–0.5% in aqueous solution. Enzymes may also be used to partially digest the tissue. Bioactive materials (e.g. heparin, aspirin, antibiotics, drugs, or anticalcification agents) may be applied to the biomaterial.

(3) Sterlization—Material sterilization is essential for medical device applications. Suitable methods include: (a) liquid systems using GA and formaldehyde, (b) ethylene or propylene oxide, or (c) radiation with the material in the dry state following lyophilization.

(4) Bonding—Bonding of the biomaterial to polymer substrates is an optional step. The method may be applied to both processed and fresh tissue.

By this method, a piece of tissue material is first lyophilized. A layer of polymer solution (high polymer in solvent) is applied to the non-mesothelial surface and allowed to air dry. Polymer transport into the bulk tissue takes place, and a film is formed on the tissue surface following solvent evaporation. The rate of penetration is controlled by polymer concentration, solvent volatility. evaporative conditions, diffusion, and the volume applied.

In general, the first application of polymer wets the surface. Subsequent applications to build up a thicker layer do not spread, indicating the presence of a polymer surface. After the desired film thickness is established, the material is rehydrated in aqueous media. Typical polymer concentrations range from 0.5–10%.

The method is applicable to a variety of polymer/solvent systems. For example, polyurethanes may be dissolved in tetrahydrofuran, dimethylacetamide, or methylene chloride. Polyesters may be applied in hexafluoroisopropanol or o-chlorophenol.

Reacting systems may also be used, where polymer is formed following application to the tissue surface. Thus, both hard and soft substrates may be formed by a variety of polymer systems.

II
EXAMPLES OF MATERIAL PREPARATION
EXAMPLE 1

Peritoneum was taken by blunt dissection from the abdominal cavity of calves. The tissue was cleaned in PBS, pinned to a polyethylene surface, and exposed to 1% GA in PBS for 24 hours at room temperature. This was followed by 2% hydrogen peroxide for 30 min., and storage in 50% ethyl alcohol/water (50% EtOH).

EXAMPLE 2

Abdominal wall parietal peritoneum was collected by blunt dissection and tanned in 0.5% GA in PBS/3 days, then stored in 50% EtOH.

EXAMPLE 3

Calf peritoneum and pericardium were both treated using 0.5% GA/PBS for 4 days and stored in 50% EtOH.

EXAMPLE 4

Calf diaphram derived peritoneum tanned in 0.5% GA for 6 days, and stored in 50% EtOH.

EXAMPLE 5

Calf diaphram peritoneum tanned on a frame in 0.5% GA for 2 days. The material was rinsed in water and then freeze dried at $-30°$ C., $5 \times 10^{-2}$ torr for 1.5 hrs. Solutions of 3% and 6% Tecoflex** polyurethane (solution grade SG-80A) in tetrahydrofuran were applied to the non-mesothelial surface. Additional layers were cast, allowing each coat to fully dry. After 24 hours, the tissue was rehydrated in water.
(** Registered Trade Mark)

EXAMPLE 6

Calf diaphram paritoneum was tanned in 0.5% GA/PBS for 5 days. After rinsing in PBS, 15cm² pieces were placed in 500 ml of 0.1. 0.5, and 1% hexanediamine in 0.1M citrate/phosphate buffer at pH 5.6. After 24 hours, the material was rinsed in water and stored in 50% EtOH.

EXAMPLE 7

Calf diaphram peritoneum tanned for 6 days in 0.5% GA (50cm² samples) was rinsed in 500 ml PBS for 5 min. Three samples were then placed in 500 ml THF to dehydrate. After 6 hours, one sample each was placed into 500 ml of 0.1. 0.5. and 1% dicyclohexylmethane diisocyanate in THF (Tecoflex** Grade 2-80A) for 24 hours, The material was then rinsed in 500 ml water for 5 min. then 30 min. in fresh water, then stored in 50% EtOH.

III MATERIAL CHARACTERIZATION

A series of in vitro tests were conducted on the biomaterials produced by the methods described.

Comparative light level histologic analysis was performed between Example 3 and peritoneum removed in a similar manner and fixed in picric acid-formaldehyde (PAF). Both tissues were paraffin embedded, 5µ sectioned, and stained with Hematoxylin and Eosin, and Verhoeff's elastin stains. A dense fibro-elastic structure was observed which containes zones of blood vessels. A single layer of mesothelial cells were well preserved on the surface. Stains for elastin show a dense mixture of fibrous and elastin fibers in a multidirectional arrangement. No significant morphologic differences were seen between the two samples. The preparation methods used preserved fine cellular detail as evidenced by the varied chromatin pattern of the nuclei and the absence of clefting or fragmentation.

Scanning electron microscopy showed a clean confluent layer of mesothelial cells. Minor cracks on the surface were considered associated with stretching of the fresh tissue prior to fixation. The non-mesothelial surface revealed a multilayered and semidirectional collection of collagen fibers. At 180x the wavy nature of the fibers was evident.

Transmission electron microscopy was also performed, and revealed a dense pattern of elastin fibers and tight bundles of collagen fibrils. Fine structure preservation was also evident in intracellular details.

Tensile Properties—The uniaxial tensile properties by Example 3 were determined and compared with pericardium identically processed. Test specimens were 1cm wide and approximately 0.2 mm thick. The raw data are given in Table 1. Samples A and B are peritoneum tested parallel and perpendicular to the collagen fiber directions. Samples C, D, and E are the parallel, perpendicular, and 45° pericardial samples. Data points are the averages of two runs.

TABLE 1

| Applied Force (g) | Percent Strain | | | | |
|---|---|---|---|---|---|
| | A | B | C | D | E |
| 15.13 | 2.1 | 5.2 | 1.4 | 3.4 | 4.5 |
| 30.86 | 4.2 | 9.5 | 2.6 | 6.0 | 7.4 |
| 46.22 | 6.5 | 12.6 | 3.8 | 7.3 | 9.0 |
| 64.44 | 8.3 | 17.4 | 4.0 | 9.0 | 11.2 |
| 82.92 | 10.6 | 20.9 | 4.5 | 10.6 | 12.5 |
| 101.60 | 11.6 | 24.2 | 5.3 | 12.2 | 13.7 |

These data indicate the peritoneal material to be more extensible than pericardium. Considerable anisotropy is also indicated, though somewhat less than pericardium. With proper material orientation, it may be possible to construct valve prostheses with leaflet flexion taking place perpendicular to the collagen fiber direction, thereby minimizing material delamination.

Thermal Contraction—The thermal shrinkage of collagen is essentially a melting phenomena, occuring in the vicinity of 60° C. for virtually all mammalian collagens (12). Crosslinking can raise the shrinkage temperature by as much as 30° C. The thermal characteristics of bioprosthetic materials have been used as a general measure of crosslinking. The shrinkage temperature was determined from visual observation of tissue samples suspended in PBS and slowly heated at 2° C. per minute. Table 2 lists representative data.

TABLE 2

| Sample | Shrink Temp. °C. |
| --- | --- |
| Ex. 1 | 83.5 |
| Ex. 7 (.1%) | 87.0 |
| (1%) | 86.7 |
| A | 86.5 |
| B | 87.0 |
| C | 87.0 |
| Fresh | 66.5, 67.5 |

Samples A,B, and C are peritoneal samples fixed for 1 day in 0.5% GA and stored in 50% EtOH. The samples treated with diamine have the same visual shrinkage characteristics. This is not surprising, as direct isometric tension measurements are usually needed to verify such differences. Values of 82°-84.5° C. are reported for GA tanned bovine pericardium, and approximately 85° C. for GA tanned porcine aortic valve cusps (13).

Collagen Content—The collagen content of the peritoneal biomaterial was determined by measuring the hydroxyproline content (14). Table 3 lists the percentage collagen on a dry weight basis.

TABLE 3

| Sample | Percent Collagen |
| --- | --- |
| Ex. 3 | 27.8 38.0 |
| Ex. 4 | 32.1 40.5 |
| A | 50.6 57.4 |
| B | 34.0 |

These collagen values are in the range expected of connective tissues serving as the primary structural component of biomaterials. Samples A and B were tanned in 0.5% GA for 3 days and 1 day respectively.

Surface Properties—Surface tension measurements have proven to be useful parameters in screening potential blood contacting biomaterials. The critical surface tension is defined as the liquid surface tension below which complete spreading occurs on a surface. The solid surface free energy may more accurately be described with polar and dispersive components (15). Table 4 lists the data obtained on Example 3 from contact angle measurements using a series of highly purified organic liquids of known surface tension. Data are in dynes/cm².

TABLE 4

|  | MS | NMS |
| --- | --- | --- |
| Critical surface tension | 32.3 | 35.7 |
| Dispersive component | 22.4 | 25.5 |
| Polar component | 22.7 | 23.4 |

The critical surface tension values are in the high range expected of tissue materials, possibly due to the presence of lipoidal material on the surface. The polar and dispersive component values however are well within the desired range as well as indicating the desired balance between these two surface energy factors.

Multiple attenuated infra red (MAIR) spectroscopy was performed on Example 3. This technique records the surface IR spectra and gives semiquantitative data on the presence of major biochemical groups. The MAIR spectra show the presence of amide I and II bands demonstrating the predominance of surface protein. Minor amounts of glycoprotein and carbohydrate are present at levels usually seen on connective tissue and vascular surfaces. A higher than normal loval of lipid was observed, later confirmed by visual observation. Improved methods of tissue collection have reduced this to an acceptable level.

Analysis of Bonded Materials—A sample of Example 5 was ethanol dehydrated, stained with osmium and Toluidine Blue, embedded in Maraglas, and sectioned at 1μ. Light microscopy showed the polyurethane to have uniformly penetrated half way through the tissue and formed a layer on the surface. Normal histologic structure was retained by the tissue. The region of penetration appeared to consist of an integral tissue/polymer composite.

In summary, these data show the peritoneal biomaterial to have structural, biochemical, surface, and crosslinked properties suitable for biomaterial application.

The material produced in accordance with the present invention has wide application in surgical treatments for the repair of defects in the body including medical devices.

IV

APPLICATIONS

Trileaflet bioprosthetic valves have been constructed using the peritoneal biomaterial. The valves have a polyester fabric covered polymer stent in the standard trileaflet configuration. In vitro performance testing is currently ongoing.

The peritoneal biomaterial may be used in cardiovascular applications for vascular patching, holes in the heart, or periocardial defects. In tubular form, vascular grafts may be fabricated. Other applications include heart valves, ventricular assist devices, or artificial hearts.

Burn and/or wound dressings may be produced.

For general surgical applications, the biomaterial may be used for hernial repair or as an aid in gastronintestinal anastomoses.

Conjunctival replacements may be produced using a thin membrane. Optical clarity may be achieved by treating the material with oxidizing agents such as hydrogen peroxide or hypochlorite.

Polymer backed tissues may be used to fabricate artificial heart components. The polymer binding method may also be applied to other biological materials. As an outer coating on vascular grafts, added strength and resistance to aneurysm formation may be imparted. Fatigue resistance may also be imparted to existing bioprosthetic heart valves.

The bonding method is also suitable for providing a biocompatible (tissue) surface to existing polymer systems, especially for blood contacting applications.

REFERENCES

1. Dardik, H. "Arterial Grafts: 1900-1978", Graft Materials in Vascular Surgery, Year Book Medical Publishers, Chicago, Ill., Chap. 1, pp. 3-12 (1978).
2. Voorhees, A. B., et al., "Use of tubes constructed from Vinyon-N cloth in bridging Arterial Defects," Ann. Surg. 135;332 (1952).
3. Wright, C. B. ed. Vascular Grafting, John Wright Pub., Littleton, MA. Section II Large Vessel Grafts, pp. 27-52 (1983).
4. Dardik, H. Et al., "Biodegradation and Aneurysm Formation in Umbilical Vein Grafts," Ann. Surg. 199(1); 61-68 (1984).
5. Binet, J. P. et al., "Clinical use of Heterografts for replacement of aortic valve," J. Thorac. Cardiovas. Surg. 55; 238-242 (1968).

6. Ionescu, M. I. et al., "Heart valve replacement with the Ionescu-Shiley pericardial xenograft," J. Thorac. Cardiovas. Surg. 73; 31–42 (1977).

7. Morse, D. ed. "Guide to Prosthetic Heart Valves," Springer-Verlag, New York (1985), pp. 225–232.

11. Fadadi, A. M. et al., "The Use of Autogeneous Peritoneum for Heart Valve Replacement," J. Thorac. Cardiovas. Surg., 60(2): 188–195 (1970).

12. Flory, P. J. et al., "Melting Equilibrium for Collagen Fibers Under Stress," J. Am. Chem. Soc., 83:1308–1316 (1961).

13. Ionescu, M. I. ed., "Tissue Heart Valves," Butterworths, London, 1978, pp. 349–352.

14. Stegman, H. "Mikrobestimmung von Hydroxyprolin mit Chloramin-T und P-Dimethylaminobenzaldehyde," Z. Physiol. Chem. 187:41 (1958).

15. Nyilas, E., et al., "Effects of Polymer Molecular Structure and Force-Field Characteristics on Blood Interfacial Phenomena. I." J. Biomed. Mater. Res. Symp. No. 8, pp. 51–68 (1977).

16. U.S. Pat. No. 4,167,045 (Sawyer).

17. U.S. Pat. No. 3,974,526 (Dardik).

I claim:

1. A biomaterial suitable for use in medical devices which comprises peritoneal tissue which has been chemically treated to crosslink the collagen in the tissue.

2. A biomaterial as claimed in claim 1, wherein the tissue is animal parietal peritoneum tissue.

3. A biomaterial as claimed in claim 1, which comprises peritoneal tissue treated in accordance with claim 1, bonded to a synthetic substrate.

4. A method for processing animal peritoneal tissue into biomaterial suitable for use in medical devices, wherein the tissue is chemically treated to crosslink the collagen and make the tissue stable, less antigenic, and sterile.

5. A method as claimed in claim 4, wherein the tissue is treated with a tanning agent to effect crosslinking.

6. A method as claimed in claim 5, wherein the tanning agent is selected from the group consisting of glutaraldehyde, formaldehyde, carbodiimides, diisocyanates, and adipic dialdehyde.

7. A method as claimed in claim 5, wherein the tanning agent is glutaraldehyde.

8. A method as claimed in claim 7, wherein the tissue is treated with a diamine in addition to the glutaraldehyde treatment.

9. A method as claimed in claim 5, wherein the tissue is sterilized after the crosslinking treatment.

10. A method as claimed in claim 9, wherein sterilization is effected by treatment with (a) formaldehyde, (b) ethylene or propylene oxide, or (c) radiation.

11. A method for producing a biomaterial as claimed in claim 3, which comprises lyophilizing the crosslinked tissue and applying a solution of a polymer in an organic solvent to the tissue and allowing the solvent to evaporate.

12. A method as claimed in claim 11, wherein multiple applications of the polymer solution are made, the solvent being allowed to completely evaporate after such application.

13. A biomaterial as claimed in claim 3 wherein the synthetic substrate is a polymer which is bonded to and penetrates in the non-mesothelial surface of the peritoneal tissue.

* * * * *